United States Patent [19]

Thill et al.

[11] Patent Number: 4,597,754

[45] Date of Patent: * Jul. 1, 1986

[54] LONG CAPILLARY TUBE HOSE ASSEMBLY FOR FLUID DISPENSING DEVICE

[75] Inventors: Gary A. Thill, Vadnais Heights, Minn.; Jerome E. Strand, St. Joseph, Wis.

[73] Assignee: Minnesota Mining and Manufacturing Company, Saint Paul, Minn.

[ * ] Notice: The portion of the term of this patent subsequent to May 13, 1997 has been disclaimed.

[21] Appl. No.: 577,757

[22] Filed: Feb. 7, 1984

Related U.S. Application Data

[60] Continuation-in-part of Ser. No. 317,257, Nov. 2, 1981, Pat. No. 4,430,079, and a continuation-in-part of Ser. No. 144,614, Apr. 28, 1980, Pat. No. 4,298,000, which is a division of Ser. No. 958,678, Nov. 8, 1978, Pat. No. 4,202,333.

[51] Int. Cl.$^4$ .................... A61M 37/00; A61M 1/00; A61M 5/14; A61M 5/20

[52] U.S. Cl. .................... 604/154; 604/151; 604/152; 604/153; 604/155; 604/81; 604/135; 604/207; 604/236; 604/51; 604/52; 138/177; 138/118; 428/36; 141/19; 141/329; 141/330; 141/31

[58] Field of Search .................... 604/51, 52, 151–155, 604/81, 135, 207, 236; 138/177, 18; 428/36; 141/19, 329, 330, 31

[56] References Cited

U.S. PATENT DOCUMENTS

| | | | |
|---|---|---|---|
| 3,203,455 | 8/1965 | Horabin | 604/183 X |
| 3,886,938 | 6/1975 | Szabo et al. | 604/135 |
| 3,951,174 | 4/1976 | Conant | 138/115 X |
| 4,034,754 | 7/1977 | Virog | 604/81 |
| 4,059,110 | 11/1977 | Wuthrich et al. | 128/218 A |
| 4,105,029 | 8/1978 | Virog | 604/81 |
| 4,140,020 | 2/1979 | Cook | 73/864.11 X |
| 4,140,117 | 2/1979 | Buckles et al. | 604/132 |
| 4,150,672 | 4/1979 | Whitney et al. | 604/135 X |
| 4,202,333 | 5/1980 | Thill et al. | 604/135 |
| 4,430,079 | 2/1984 | Thill et al. | 604/154 |

FOREIGN PATENT DOCUMENTS 2240694  3/1973  Fed. Rep. of Germany ... 128/218 A

*Primary Examiner*—William G. Wright
*Attorney, Agent, or Firm*—Donald M. Sell; James A. Smith; William L. Huebsch

[57] ABSTRACT

A hose assembly for use to regulate flow from a dispensing device that provides a generally constant pressure on a liquid to be dispersed. The hose assembly includes a length of capillary tubing through which the liquid must pass as it is dispersed which has a length of at least 45 centimeters and a volume of less than about 0.25 cubic centimeters so that the assembly can provide a slow steady predetermined flow rate while containing a small amount of the liquid being dispensed.

7 Claims, 6 Drawing Figures

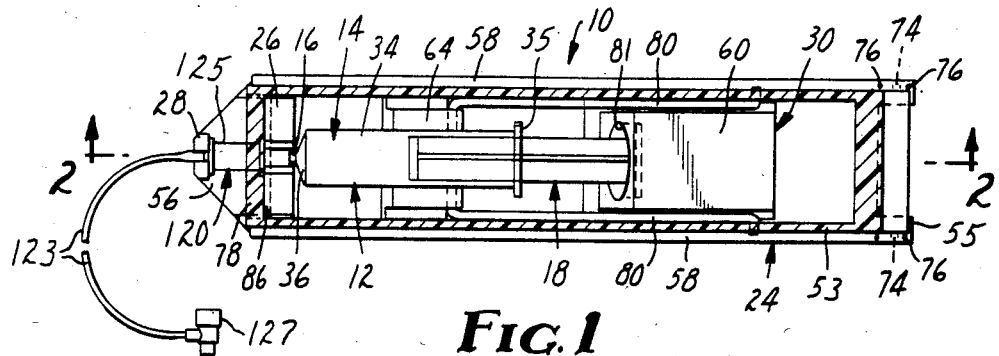
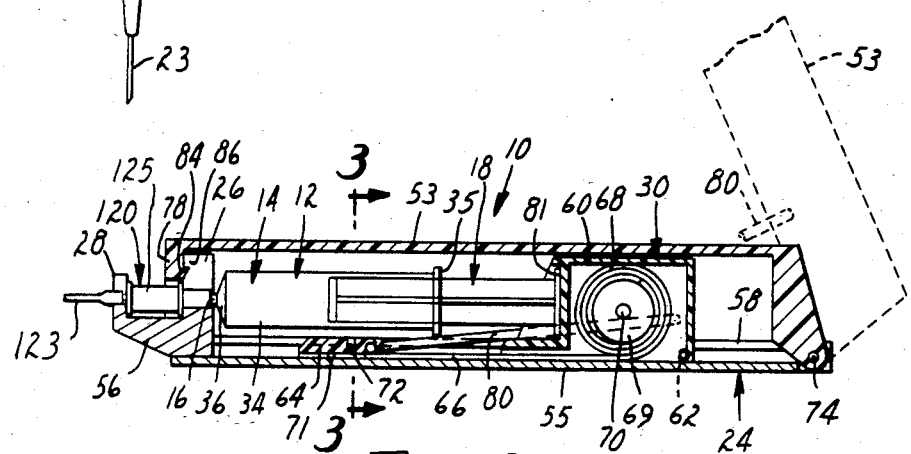
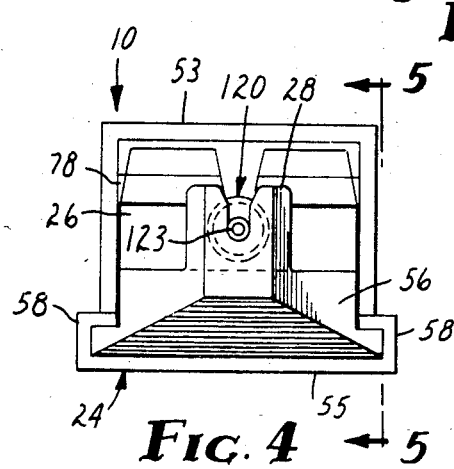
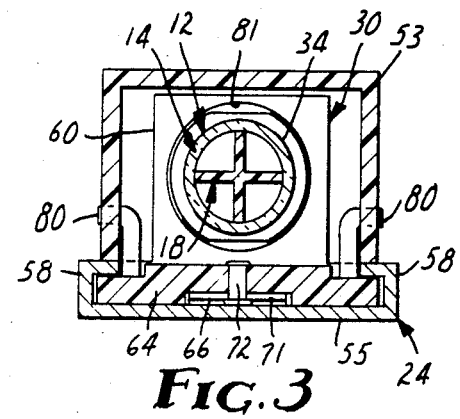

LONG CAPILLARY TUBE HOSE ASSEMBLY FOR FLUID DISPENSING DEVICE

CROSS-REFERENCE TO RELATED APPLICATIONS

This application is a continuation in part of U.S. patent application Ser. No. 317,257 filed Nov. 2, 1981, which issued on Feb. 7, 1984, as U.S. Pat. No. 4,430,079 and is a continuation in part of U.S. patent application Ser. No. 144,614, filed Apr. 28, 1980, which issued on Nov. 3, 1981 as U.S. Pat. No. 4,298,000 which is a Division of U.S. patent application Ser. No. 958,678, filed Nov. 8, 1978, which issued on May 13, 1980, as U.S. Pat. No. 4,202,333.

BACKGROUND OF THE INVENTION

The U.S. Patents listed above describe a device for dispensing fluid at a slow, uniform rate over a sustained period of time which has a simple, inexpensive structure, is easy to use, requires no regulation or adjustment by the person using the device, and which is well-safeguarded against tampering or inadvertent improper operation of the device.

The dispensing device described therein comprises a hose assembly adapted to be coupled to a conventional syringe, which hose assembly comprises a length of capillary tubing through which the fluid must pass while being delivered to a patient, and means for applying a uniform force to the plunger to provide fluid flow through the capillary tube at a slow, steady rate over a long period of time (e.g., less than 60 milliliters per hour).

As stated therein the rate of flow Q in cc/sec through the capillary tube can be estimated from Poiseuille's Law expressed in the equation:

$$Q = (Pr^4)/(8ln)$$

where P is the pressure drop through the tube in dynes/cm$^2$, r is the internal radius of the capillary tube in cm, l is the length of the capillary tube in cm, and n is the liquid viscosity in poise. By solving this equation it can be found that capillary tubes of a reasonable length suitable for restricting flow to rates in the range indicated under the influence of pressures of the range of pressures easily developed in a syringe (e.g., about 69,000 to 2,068,400 dynes/cm$^2$) can have bores in the range of about 0.0025 to 0.038 cm. With current technology it is difficult to produce capillary tubing in this size range with bore diameters which deviate less than about 10% from a nominal diameter, however. Since the rate of flow through a tube is proportional to the fourth power of its diameter, such a deviation could cause a variation of about −34% to +46% in flow rate, which would be unacceptable for most medical uses. By only using long lengths of capillary tubing, however, (i.e., capillary tubes over 2 centimeter in length) much less variation in flow rates is found between different lengths of capillary tubing than is suggested above; perhaps because diameter variations tend to cancel each other along the length of the capillary tubes. With capillary tubing of polytetrafluoroethylene sold under the trade designation "Teflon" (which is preferred) having a nominal inside diameter in the range of 0.0025 to 0.019 cm, it has been found that lengths of the capillary tubing in excess of 2 cm. normally produce flow rate variations of less than 10%, which is acceptable for medical use of the device described herein.

Hose assemblies having capillary tubes of different nominal diameters which afford different rates of fluid flow (which rates, for example, may be indicated by color coding of the hose assemblies) can be used interchangeably in the device, and the inexpensive hose assemblies can be disposed of after use to insure sanitation for medical or other uses.

One problem presented by the use of such a hose assembly is that in many instances (such as for use in introducing fluids intraveniously) prior to activating the device, air must be purged from the hose assembly to preclude air being delivered to the patient. This purging is typically done by attaching the hose assembly to the syringe outside of the device, and manually activating the syringe until liquid has entirely filled the hose assembly; after which the syringe is placed in the device and the device is activated to deliver the liquid to the patient at the desired rate.

U.S. Pat. No. 4,430,079 teaches that for hose assemblies having small diameter capillary tubing (e.g., 0.0045 to 0.01 cm) adapted to alow only very slow rates of flow (e.g. 0.5 to 15 ml/hr) it is preferred to use a first embodiment of the hose assembly that allows the capillary tubing to be bypassed to afford rapid purging of air from the hose assembly with fluid from the syringe. The first hose assembly embodiment includes a metering assembly that provides a coupler between the hose assembly and the syringe. The metering assembly includes the capillary tube and parts moveable between a metering position at which fluid flowing through the metering assembly must pass through the capillary tubing, and a purging position at which fluid propelled by manual operation of the syringe can bypass the capillary tube and flow rapidly through the metering assembly to purge the hose assembly. The device has structure that insures that the metering assembly in this first embodiment of the hose assembly is in its metering position when the dispensing device is activated to preclude operation of the device with the metering assembly in its purge position. Support means included in a frame for the device supports the metering assembly and thereby a syringe coupled to the metering assembly. The support means is specially adapted so that it will engage and support the metering assembly only when it is in its metering position.

Also U.S. Pat. No. 4,430,079 teaches that for metering devices having larger diameter capillary tubing (e.g. over 0.010 cm) adapted to allow relatively larger rates of flow (e.g. over 15 ml/hr) one of several other embodiments of the hose assembly can be used that have no by pass, in which embodiments the capillary tubing may be positioned at the end of the hose assembly opposite the syringe. When the capillary tubing is positioned at the end of the hose assembly opposite the syringe almost all of the air passes through the capillary tube before the liquid reaches it, which, because of the extremely low viscosity of air compared to liquid, allows a fairly rapid purge rate (e.g. less than about 20 seconds). These other embodiments of the hose assembly include more conventional couplers at their ends adapted to engage the syringe, which couplers are adopted to be received in the support means of the device.

When either of the above described types of hose assemblies is made in a long length (e.g., over 45 centimeters and preferably in the range of 120 to 150 centimeters), however, it has a relatively large internal volume (e.g., ½ to ¾ cubic centimeter) which is quite significant compared to the volume of the syringe from which the liquid is dispersed. Thus persons filling the syringe must add additional liquid to allow for the volume in the hose assembly (which will normally be still filled with the liquid when it is disgarded after use) while providing the intended delivered volume of liquid. This is both wasteful of the liquid, and causes an element of uncertainty in forecasting what internal volume the hose assembly will have.

SUMMARY OF THE INVENTION

The invention claimed in this application provides long length hose assemblies that can effectively meter dispensing liquid flow from the device described above without containing a significant internal volume of liquid that must be accounted for in filling of the syringe.

According to the present invention there is provided a hose assembly adapted for use with a fluid dispensing device (such as that described above) which applies a constant pressure to disperse fluid through the hose assembly. The hose assembly comprises a capillary tube defining a through passageway between ends of the hose assembly, which capillary tube has a length of at least 45 centimeters (and preferably over 120 centimeters) while having a volume of less than about 0.25 cubic centimeter.

Suprisingly, such capillary tubes can be quite quickly purged of air, and provide quite predictable flow rates, while containing such a small internal volume that no additional liquid need be added to the syringe to compensate for the liquid that is retained in the tube after its use.

BRIEF DESCRIPTION OF THE DRAWING

The device will further be described with reference to the accompanying drawings wherein like numerals refer to like parts through the several views and wherein:

FIG. 1 is a horizontal sectional view of a fluid dispensing device coupled to a hose assembly according to the present invention, which device has inserted therein a syringe from which fluid is to be dispensed through the hose assembly;

FIG. 2 is a sectional view taken approximately along line 2—2 of FIG. 1;

FIG. 3 is an enlarged sectional view taken approximately along line 3—3 of FIG. 2;

FIG. 4 is an enlarged end view of the fluid dispensing device of FIG. 1;

DESCRIPTION OF THE PREFERRED EMBODIMENT

Figure 5:
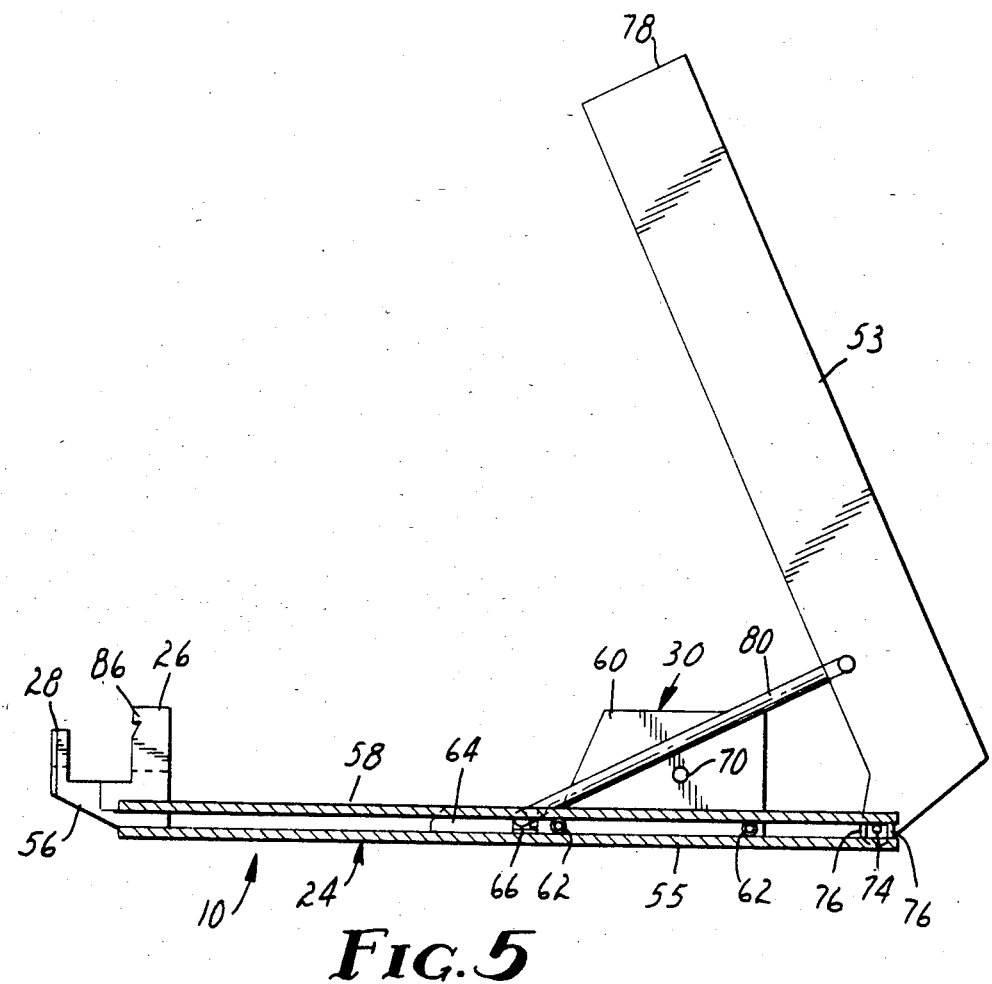
FIG. 5 is a sectional view taken approximately along line 5—5 of FIG. 4 except that a cover for the fluid dispensing device is open, and the hose assembly and the syringe are not inserted in the device.

Referring now to the drawing, there is illustrated a fluid dispensing device 10 adapted to apply a uniform pressure to a liquid to dispense the liquid through a hose assembly 120 according to the present invention.

The fluid dispensing device 10 is adapted to dispense fluid at a slow, steady rate through the hose assembly 120 over a prolonged period of time from a conventional syringe 12 of the type including an elongate housing 14 with an outlet tube 16 at one end, and a plunger 18 adapted to expel fluid within the syringe 12 through the outlet tube 16.

Generally the device 10 can be used with one of several embodiments of hose assemblies, including any of the hose assembly embodiments described in U.S. Pat. No. 4,430,079 (incorporated herein by reference) and the hose assembly 120 described herein. Like those other hose assemblies, the hose assembly 120 (see FIG. 6) has first and second ends 121 and 122, a coupler 125 at its first end 121 for coupling the hose assembly 120 to the syringe 12, and a length of capilary tubing 123 shown coupled to a needle 23 via a Luer-lock fitting 127 at its second end 122 opposite the coupler 121 to facilitate injecting the fluid into a patient's veins or tissues. Alternatively the tubing 123 could be open-ended to facilitate insertion of the tubing 123 into a patient's digestive or breathing passages or have attached thereto any shape of head via the Luer-lock fitting 127 or otherwise to facilitate distributing fluids to a patient's body. The device 10 includes a support frame 24 comprising spaced fork-like members 26 and 28 for supporting the coupler 121 and the syringe 12; and spring means 30 for applying uniform force against the plunger 18 of the syringe 12 to press it towards the fork-like members 26 and 28 and cause fluid within the syringe 12 to flow through the hose assembly 120.

The syringe 12 which the dispensing device 10 is adapted to receive is of a conventional type comprising the housing 14 which includes a tubular wall 34 having an open end 35, and an end wall 36 at its end opposite the open end 35 from which projects the outlet tube 16 which defines an outlet opening for the housing 14; and the plunger 18 which has one end portion positioned within and sealing against the inner surface of the tubular wall 34 and an opposite end portion projecting from the open end 35 of the tubular wall 34, and which can have fluid (typically a liquid) within the tubular wall 34 between the end wall 36 and the plunger 18.

Figure 6:
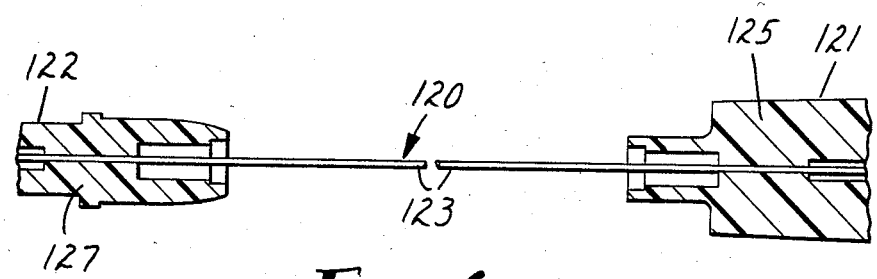
FIG. 6 is a fragmentary sectional view of the hose assembly of FIG. 1.

The hose assembly 120 used and included in the dispensing device 10 is best seen in FIG. 6. Generally, the hose assembly 120, the passageway between the ends 121 and 122 of the hose assembly 120 defined by a capillary tube 123 has an volume of less than about 0.25 cubic centimeter and a length of at least 45 centimeters, and perferably in the range of 120 to 170 centimeters; and has the coupler 125 at its first end 121. The coupler 125 is adapted for releasably attaching the hose assembly 120 to the housing of the syringe 12 with the outlet opening of the syringe communicating with the passageway through the hose assembly 120 and has an outer periphery shaped so that the coupler 125 will be received in the spaced fork-like members 26 and 28 of the support frame 24 for the device 10 and will be locked in the fork-like member 26 and 28 when a cover 35 for the device 10 is closed. Both ends of the capillary tube 123 pass into and are bonded within bores of the fitting 127 and the coupler 125 to secure the ends of the capillary tube 123 thereto.

Purging of such a hose assembly 120 in the manner described above proceeds quite rapidly because of the relatively small amount of air that must be displaced.

The device 10 includes activating means manually operated by movement of the cover 53 and coupled to the spring means 30 for allowing the syringe 12 and attached hose assembly 120 to be easily inserted in or removed from the device 10 by moving the spring means 30 to a disengaged position relative to the syringe 12 when the cover 53 is opened, and by moving the spring means 30 to an engaged position against the plunger 18 of the syringe 12 when the cover 53 is closed, and means for securing the syringe 12 and hose assembly in the device 10 when the cover 53 is closed so that they may not be tampered with when the spring means is applying a uniform force to expel fluid from the syringe 12.

The frame 24 includes an elongate bar-like base portion 55 at one end of which is fixed a support member 56 including the spaced fork-like members 26 and 28 which are disposed so that they will position the syringe 12 attached to the coupler 125 received in the fork-like members 26 and 28 over and parallel to the base portion 55. The bar-like base portion 55 has upstanding opposed generally L-shaped rails 58 along its edges between which a hollow block 60 is mounted for movement longitudinally of the base portion 55 via four rollers 62 projecting from the edges of the block 60 adjacent the base portion 55. A plate-like slide 64 is also mounted between the rails 58 for sliding movement longitudinally of the base portion 55 between the block 60 and the member 56. A spring 66 of the type having the registered tradename "Neg'ator" has a portion 68 coiled about a hub 69 rotatably mounted within the block 60 on a shaft 70, and a straight end portion 71 extending from the block 60 to the slide 64 where it is attached by a rivet 72. The "Neg'ator" spring 66 provides a constant force attempting to wrap the entire length of the spring 66 onto its coiled portion 68, and thus provides a constant force biasing the block 60 toward the slide 64.

The cover 53 is a rectangular box-like member of rigid transparent plastic material (preferably polysulfone) having an open side disposed adjacent the base portion 55 and having opposite outwardly projecting trunnions 74 on its end opposite the support member 56 which are pivotably mounted between the rails 58 and two pins 76 spaced along each of the rails 58 to afford pivotal movement of the cover 53 from an open position spaced from the base member 55, block 60 and syringe 12 (FIG. 5); and a closed position adjacent the base member 55 enclosing the block 60 and the syringe 12 therebetween, and with an edge portion 78 of the cover 53 against the coupler 125 received in the fork-like members 26 and 28 to preclude their removal (FIG. 2), at which closed position the cover 53 will be retained by releasable latch means later to be explained. Parallel links 80 are pivotably mounted at their ends between the cover 53 and the slide 64, and are sized and disposed so that moving the cover 53 to its open position (FIG. 5) will move the slide 64 and block 60 to a position sufficiently spaced from the fork-like members 26 and 28 that the metering assembly 20 and attached syringe 12 may be inserted in or removed therefrom; and that moving the cover 53 to its closed position (FIG. 2) will move the slide 64 adjacent the support member 56 so that when the syringe 12 and attached coupler 125 are supported from the fork-like members 26 and 28, the block 60 will engage the plunger 18 on the syringe 12 during such movement with the end of the plunger received in a centering pocket 81 in the adjacent face of the block 60. Such engagement will cause the slide 64 to separate from the block 60 in opposition to the spring 66 so that while the cover 53 is closed, the spring 66 will apply a constant force against the plunger 18. Also while the cover 53 is closed, the edge portion 78 rests transversely against the coupler 125 and precludes its removal from between the fork-like members 26 and 28.

The means for releasably latching the cover 53 in its closed position comprises transverse mating hook-like lips 84 and 86, one of which lips 84 is a part of the cover 53 adjacent its edge portion 78, and the other of which lips is a part of the fork-like member 26 adjacent its distal end; the spring 66; and a spacing between the pins 76 that allows limited longitudinal movement of the cover 53 relative to the base portion 55 of the frame 24. When the cover 53 is being moved to its closed position and after the block 60 engages the plunger 18 of the syringe 12, the force applied by the spring 66 between the separated block 60 and slide via the links 80 will press the trunnions 74 on the cover 53 against the pins 76 opposite the support member 56. As the cover 53 approaches its closed position, cam surfaces on the lips 84 and 86 engage to move the center portion of the cover 53 toward the support member 56 and allow the hook-like lips 84 and 86 to pass each other, whereupon the spring 66 again moves the center portion of the cover 53 away from the support member 56 to engage the lips 84 and 86 as the cover 53 reaches its fully closed position. Opening the cover 53 then requires sliding it longitudinally toward the support member 56 against the bias of the spring 66 to disengage the lips 84 and 86 before the cover can be pivoted to its open position, which opening operation is not apparent from a casual inspection of the closed cover 53 and could deter unauthorized deactivation of the device 10. Alternately the means for latching the cover 53 in its closed position could be a more conventional self-latching push button release latch between the cover 53 and base portion 55.

As an example of the use of the fluid dispensing device 10, a person first fills the syringe 12 with a fluid to be dispensed. Next he attaches the hose assembly 120 to the syringe 12, and manually activates the syringe 12 so that fluid flows rapidly through the hose assembly and purges air from it. Next the user presses the coupler 125 between the fork-like members 26 and 28 with the syringe 12 projecting over the base portion 55. The user then couples the part of the fitting 122 on the hose assembly 120 with the part on the needle 23 or a cannula (not shown) which he has previously inserted in a patient's vein or tissues, and moves the cover 53 toward its closed position so that the cover 53 via the links 80, slide 64, and spring 66 moves the block 60 into engagement with the plunger 18 on the syringe 12, after which the slide 64 is separated from the block 60 so that the spring 66 will apply a force against the plunger 18. Further movement of the cover 53 to its closed position will cause the lips 84 and 86 on the cover 53 and fork-like members 26 to cam past each other whereupon the spring 66 will maintain the lips 84 and 86 in engagement to latch the cover 53 closed. In this condition, the "Neg'ator" spring 66 will continue to apply a uniform force to cause fluid to flow at a slow uniform rate from the syringe 12 through the hose assembly 120 and needle 23 or cannula into the patient. During this time the device 10 can be positioned in any attitude or carried on the patient to afford ambulation without affecting the fluid dispensing rate. Also tampering with the syringe 12 or hose assembly 120 while the fluid is being dispensed is precluded since the syringe 12 is enclosed by the cover 53, and the coupler 125 is locked between the fork-like members 26 and 28 by the edge portion 78 of the cover, and anyone attempting to gain access to the syringe 12 or to remove the coupler 125 will have to open the cover 53, thereby deactivating the device 10.

The present invention and its use have been explained with respect to one general type of medical use. The device may, however, be used in ways other than that indicated both for medical or other uses. For example, one or more of the devices 10 may be used to dispense fluids into a standard intravenous administration set. Also, the fluid dispensing device 10 may be used in industrial applications such as to introduce chemicals such as a catalyst into fluids moving through a continuous process, or for other uses where a small continuous supply of fluids is needed. Thus the scope of the invention should not be limited by either the structure or use of the embodiment described herein, but should be determined only by the scope of the dependent claims.

What is claimed is:

1. A fluid dispensing device adapted for engaging a fluid-filled syringe to dispense fluid from the syringe at a slow, steady rate of less than 60 cubic centimeters per hour, said syringe being of the type comprising an elongate housing including a tubular wall having an open end and an end wall having an outlet opening at the end of the tubular wall opposite its open end, and a plunger having one end portion positioned within and sealing against the inner surface of said tubular wall and an opposite end portion projecting from the open end of said tubular wall, with the fluid being within said tubular wall between said end wall and said plunger, said device comprising:

a hose assembly having first and second ends and comprising a capillary tube defining a passageway between said ends, said capillary tube having a volume of less than about 0.25 cubic centimeter and a length of at least about 45 centimeters, and said hose assembly further including a coupler at said first end adapted for releasably attaching said for the capillary tubing to the housing of a said syringe with the outlet opening of the syringe communicating with said passageway;

a frame comprising support means adapted for engaging and supporting said coupler;

spring means adapted for applying a uniform force against the plunger of the syringe to cause fluid within said syringe to flow through said hose assembly; and activating means for moving said spring means between a disengaged position spaced from the plunger of a said syringe attached to said coupler to afford insertion or removal of the syringe and said hose assembly, and an engaged position engaged with said plunger to apply said uniform force, said activating means including securing means for securing the syringe and the coupler of said hose assembly in said support means when said activating means positions said spring means in said engaged position.

2. A fluid dispensing device according to claim 1 wherein said capillary tube is over 120 centimeters long.

3. A fluid dispensing device according to claim 1 wherein said is in the range of 120 to 150 centimeters long.

4. A fluid dispensing device according to claim 1 wherein:

said support frame includes an elongate portion extending away from said support means;

said support means are adapted to position a said syringe attached to said coupler over said elongate portion;

said spring means comprises a block mounted for movement along said elongate portion and having a surface adjacent said support means adapted to engage the plunger in a said syringe and a slide slideably mounted between said block and said support means for movement along said elongate portion with said spring means being coupled between said block and said slide for applying a constant force biasing said block toward said support means upon separation of said slide and said block; and said activating means comprises a cover adapted to enclose said block and a said syringe engaged with said coupler over said elongate portion said cover having one end pivotably mounted at the end of said elongate portion opposite said support means and being pivotable between an open position spaced from said elongate portion to afford insertion and removal of said coupler and a said syringe attached thereto and a closed position enclosing said block and the syringe with a portion of said cover providing said securing means, links coupled between said cover and said slide for moving said slide and block to a position spaced from the syringe when said cover is in its open position, and for moving said block into engagement with said syringe to separate said slide from said block and apply said uniform force upon movement of said cover to its closed position, and means for releasably latching said cover in its closed position.

5. A hose assembly adapted for use with a fluid dispensing device which applies a generally constant pressure to dispense fluid throught the hose assembly, said hose assembly comprising a capillary tube having first and second ends and defining a through passageway between said ends, said capillary tube having a volume of less than about 0.25 cubic centimeter and a length of at least 45 centimeters; and said hose assembly further including a coupler at said first end adapted for releasably attaching said hose assembly to a said device with an outlet opening of the device communicating with said through passageway.

6. A hose assembly according to claim 5 wherein said capillary tube is over 120 centimeters long.

7. A hose assembly according to claim 5 wherein said capillary tube is in the range of 120 to 150 centimeters long.

* * * * *